(12) United States Patent
Wang et al.

(10) Patent No.: US 8,614,224 B2
(45) Date of Patent: Dec. 24, 2013

(54) SINOMENINE DERIVATIVES AND PROCESSES FOR THEIR SYNTHESIS

(75) Inventors: Peter X. Wang, Clarkson Valley, MO (US); Tao Jiang, St. Louis, MO (US); Gary L. Cantrell, Troy, IL (US); David W. Berberich, St. Peters, MO (US); Bobby N. Trawick, Florissant, MO (US); Subo Liao, Ballwin, MO (US); John Brandt, St. Charles, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

(21) Appl. No.: 13/352,668

(22) Filed: Jan. 18, 2012

(65) Prior Publication Data

US 2012/0116086 A1 May 10, 2012

Related U.S. Application Data

(62) Division of application No. 12/316,846, filed on Dec. 17, 2008, now Pat. No. 8,461,337.

(60) Provisional application No. 61/014,099, filed on Dec. 17, 2007.

(51) Int. Cl.
*A61K 31/485* (2006.01)
*C07D 489/02* (2006.01)

(52) U.S. Cl.
USPC .......................................... 514/282; 546/44

(58) Field of Classification Search
None
See application file for complete search history.

(56) References Cited

U.S. PATENT DOCUMENTS

| 4,272,541 | A | * | 6/1981 | Kotick et al. ................. 514/282 |
| 4,543,256 | A | | 9/1985 | Neumeyer |
| 4,613,668 | A | | 9/1986 | Rice |
| 2011/0015219 | A1 | | 1/2011 | Trawick et al. |

FOREIGN PATENT DOCUMENTS

| CN | 1785976 | 6/2006 |
| DE | 289274 | 5/1915 |
| JP | 60226883 | 11/1985 |
| JP | 04504861 | 8/1992 |
| JP | 2001518444 | 10/2001 |
| JP | 2006509755 | 3/2006 |
| WO | 91/05768 | 5/1991 |
| WO | 99/02529 | 1/1999 |
| WO | 2004048340 | 6/2004 |
| WO | 2006098855 | 9/2006 |
| WO | 2009078987 | 6/2009 |

OTHER PUBLICATIONS

Grant & Hackh's Chemical Dictionary (5th Ed. 1987) at p. 148.

* cited by examiner

*Primary Examiner* — Michael Barker

(57) ABSTRACT

The invention generally provides processes and intermediate compounds useful for the production of sinomenine derivatives. In particular, the process may encompass synthetic routes for the production of (+)-sinomenine derivatives and their intermediates.

21 Claims, No Drawings

SINOMENINE DERIVATIVES AND PROCESSES FOR THEIR SYNTHESIS

CROSS-REFERENCE TO RELATED APPLICATION

This patent application is a divisional application of U.S. patent application Ser. No. 12/316,846 (filed on Dec. 17, 2008), which claims priority from Provisional Patent Application Ser. No. 61/014,099 (filed on Dec. 17, 2007), the contents of which is hereby incorporated by reference in its entirety.

FIELD OF THE INVENTION

The present invention generally relates to processes and intermediate compounds useful for the production of sinomenine derivatives.

BACKGROUND OF THE INVENTION

Sinomenine, an alkaloid isolated from the root of *Sinomenium acutum*, has been reported to possess anti-inflammatory, analgesic, blood pressure lowering, and anti-arrhythmia activities. Both the isolated molecule and the *S. acutum* plant have been used clinically in China for the treatment of rheumatoid arthritis. Although sinomenine relieves the symptoms of rheumatoid arthritis, it has some undesirable side effects. It is possible, therefore, that compounds with structures related to sinomenine would be more effective clinically, while having fewer untoward effects.

SUMMARY OF THE INVENTION

One aspect of the invention encompasses a compound comprising Formula (I):

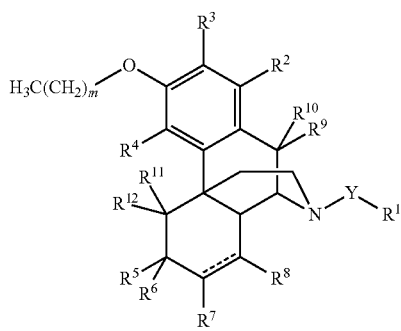

(I)

wherein:

$R^1$ is selected from the group consisting of hydrocarbyl and substituted hydrocarbyl;

$R^2$ and $R^3$ are independently selected from the group consisting of hydrogen, halogen, OH, $NH_2$, CN, hydrocarbyl, and substituted hydrocarbyl;

$R^4$ is selected from the group consisting of hydrogen, halogen, $NH_2$, CN, hydrocarbyl, substituted hydrocarbyl, and $OR^{4a}$;

$R^{4a}$ is selected from the group consisting of hydrogen and a bond that forms part of an ether-containing ring;

$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =$CHR^{5a}$, and —$O(CH_2)_2O$—;

$R^{5a}$ is selected from the group consisting of hydrogen, halogen, hydrocarbyl, and substituted hydrocarbyl;

$R^7$ is selected from the group consisting of hydrogen and $OR^{13}$;

$R^{7a}$ is selected from the group consisting of hydrocarbyl and substituted hydrocarbyl;

$R^8$ is selected from the group consisting of hydrogen, hydrocarbyl, and substituted hydrocarbyl;

$R^9$ and $R^{10}$ are independently selected from the group consisting of hydrogen, OH, $NH_2$, SH, hydrocarbyl, and substituted hydrocarbyl, wherein $R^9$ and $R^{10}$ together may form a group selected from the group consisting of =O and =S;

$R^{11}$ and $R^{12}$ are independently selected from the group consisting of hydrogen, OH, halogen, hydrocarbyl, and substituted hydrocarbyl;

Y is selected n is from the group consisting of alkyl, substituted alkyl, carbonyl, and alkyl carbonyl;

m is an integer from 0 to 8; and

----- is a single bond or a double bond.

An additional aspect of the invention encompasses a process for preparing a compound comprising Formula 3. The process comprises contacting a compound comprising Formula 2 with a compound selected from the group consisting of vinyl chloroformate and 1-chloroethyl chloroformate, followed by hydrolysis of the reaction mixture in the presence of a proton donor or a proton acceptor to form the compound comprising Formula 3 according to the reaction scheme:

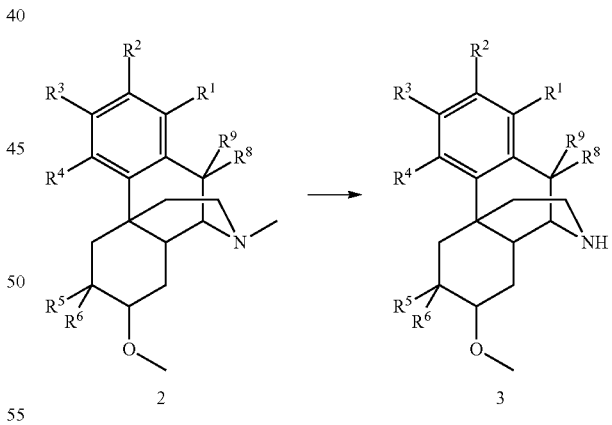

wherein $R^1$, $R^2$, $R^3$, and $R^4$ are independently selected from the group consisting of hydrogen, halogen, OH, $NH_2$, CN, hydrocarbyl, and substituted hydrocarbyl;

$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =$CHR^{5a}$, and —$O(CH_2)_2O$—; and $R^{5a}$ is selected from the group consisting of hydrogen, halogen, hydrocarbyl, and substituted hydrocarbyl; and $R^8$ and $R^9$ are independently selected from the group consisting of hydrogen, OH, $NH_2$, SH, hydrocarbyl, and substituted hydrocarbyl, wherein $R^8$ and $R^9$ together may form a group selected from the group consisting of =O and =S.

A further aspect of the invention provides a process for preparing a compound comprising Formula 4. The process comprises contacting a compound having Formula 3 with a compound selected from the group consisting of $R^7YX$ and $R^7Y$ to form the compound comprising Formula 4 according to the reaction scheme:

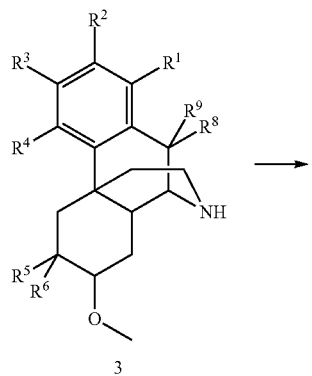

3

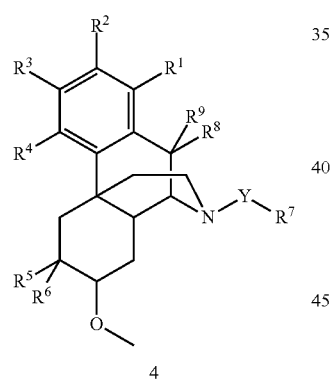

4 wherein $R^1$, $R^2$, $R^3$, and $R^4$ are independently selected from the group consisting of hydrogen, halogen, OH, $NH_2$, CN, hydrocarbyl, and substituted hydrocarbyl;

$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =CHR$^{5a}$, and —O(CH$_2$)$_2$O—; and $R^{5a}$ is selected from the group consisting of hydrogen, halogen, hydrocarbyl, and substituted hydrocarbyl.

$R^7$ is selected from the group consisting of hydrocarbyl and substituted hydrocarbyl;

$R^8$ and $R^9$ are independently selected from the group consisting of hydrogen, OH, $NH_2$, SH, hydrocarbyl, and substituted hydrocarbyl, wherein $R^8$ and $R^9$ together may form a group selected from the group consisting of =O and =S;

X is halogen; and

Y is selected n is from the group consisting of alkyl, substituted alkyl, carbonyl, and alkyl carbonyl.

An additional aspect of the invention provides a process for preparing a compound comprising Formula 5. The process comprises contacting a compound having Formula 4a with X to form the compound comprising Formula 5 according to the reaction scheme:

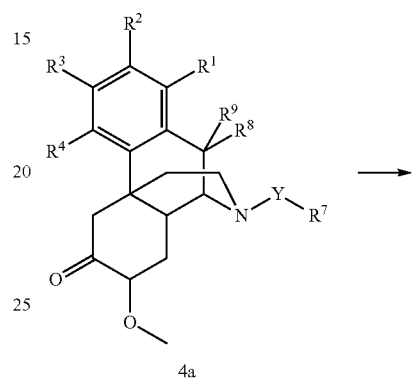

4a

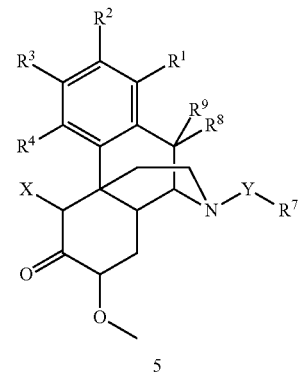

5 wherein $R^1$, $R^2$, $R^3$, and $R^4$ are independently selected from the group consisting of hydrogen, halogen, OH, $NH_2$, CN, hydrocarbyl, and substituted hydrocarbyl;

$R^7$ is selected from the group consisting of hydrocarbyl and substituted hydrocarbyl;

$R^8$ and $R^9$ are independently selected from the group consisting of hydrogen, OH, $NH_2$, SH, hydrocarbyl, and substituted hydrocarbyl, wherein $R^8$ and $R^9$ together may form a group selected from the group consisting of =O and =S;

X is halogen; and

Y is selected n is from the group consisting of alkyl, substituted alkyl, carbonyl, and alkyl carbonyl.

A further aspect of the invention provides a process for preparing a compound comprising Formula 6. The process comprises contacting a compound having Formula 5a with a proton acceptor to form the compound comprising Formula 6 according to the reaction scheme:

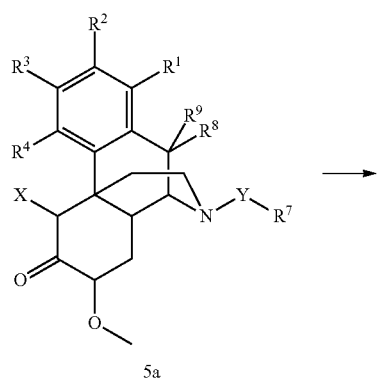

5a

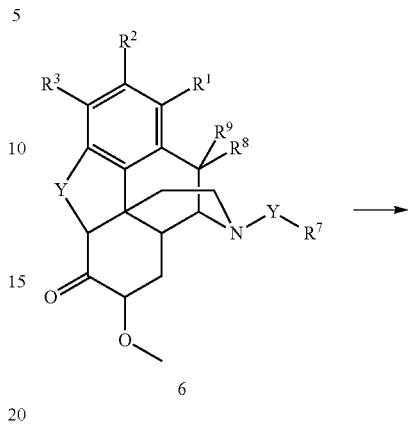

6 comprises contacting a compound having Formula 6 with a scavenger and a proton donor to form the compound comprising Formula 7 according to the reaction scheme:

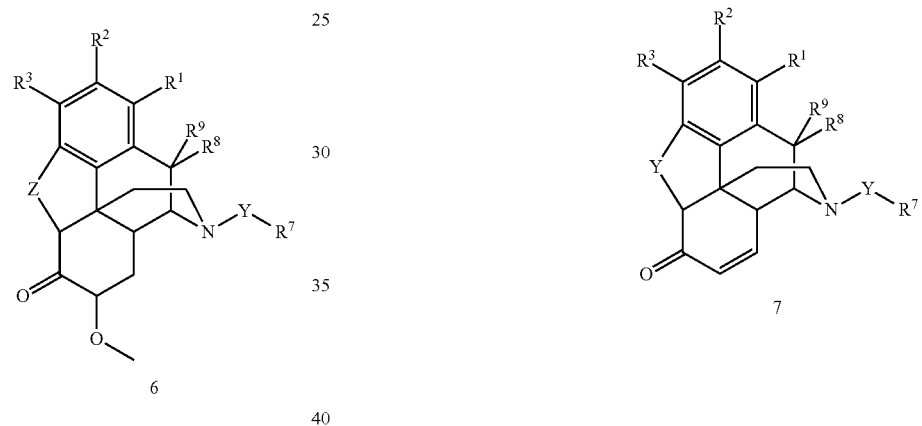

wherein
$R^1$, $R^2$, and $R^3$ are independently selected from the group consisting of hydrogen, halogen, OH, $NH_2$, CN, hydrocarbyl, and substituted hydrocarbyl;
$R^4$ is selected from the group consisting of OH and $NH_2$;
$R^7$ is selected from the group consisting of hydrocarbyl and substituted hydrocarbyl;
$R^8$ and $R^9$ are independently selected from the group consisting of hydrogen, OH, $NH_2$, SH, hydrocarbyl, and substituted hydrocarbyl, wherein $R^8$ and $R^9$ together may form a group selected from the group consisting of =O and =S; and
X is halogen;
Y is selected from the group consisting of alkyl, substituted alkyl, carbonyl, and alkyl carbonyl; and
Z is selected from the group consisting of {—}O{—} and {—}NH{—}.

Another aspect of the invention encompasses a process for preparing a compound comprising Formula 7. The process wherein
$R^1$, $R^2$, and $R^3$ are independently selected from the group consisting of hydrogen, halogen, OH, $NH_2$, CN, hydrocarbyl, and substituted hydrocarbyl;
$R^7$ is selected from the group consisting of hydrocarbyl and substituted hydrocarbyl;
$R^8$ and $R^9$ are independently selected from the group consisting of hydrogen, OH, $NH_2$, SH, hydrocarbyl, and substituted hydrocarbyl, wherein $R^8$ and $R^9$ together may form a group selected from the group consisting of =O and =S;
Y is selected from the group consisting of alkyl, substituted alkyl, carbonyl, and alkyl carbonyl; and
Z is selected from the group consisting of {—}O{—} and {—}NH{—}.

An additional aspect of the invention encompasses a process for preparation of compound 7 according to the following reaction scheme:

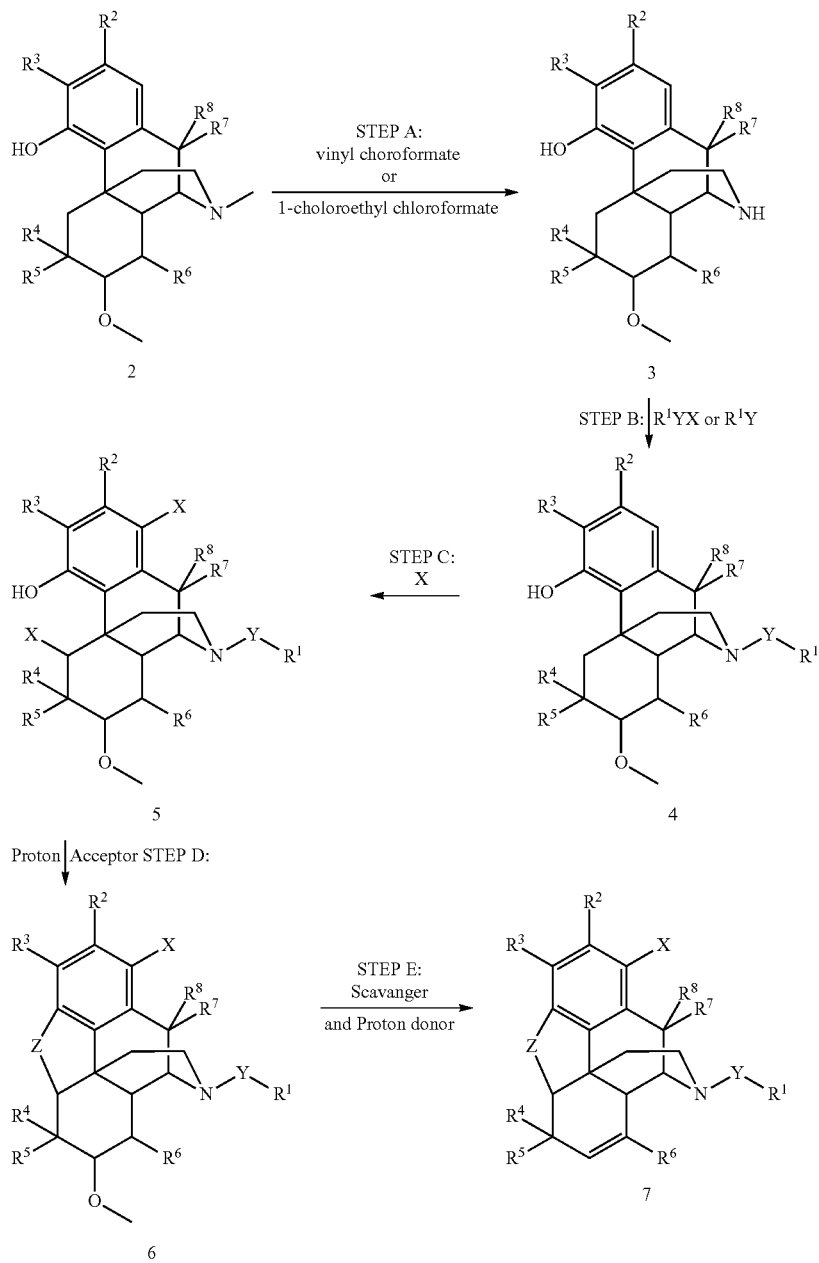

wherein:

R¹ is selected from the group consisting of hydrocarbyl and substituted hydrocarbyl;

$R^2$ and $R^3$ are independently selected from the group consisting of hydrogen, halogen, OH, $NH_2$, CN, hydrocarbyl, and substituted hydrocarbyl;

$R^4$ and $R^5$ are independently selected from the group consisting of hydrogen, OH, $NH_2$, SH, hydrocarbyl, and substituted hydrocarbyl, wherein $R^4$ and $R^5$ together may form a group selected from the group consisting of =O, =NOH, =S, =CHR$^{5a}$, and —O(CH$_2$)$_2$O—;

$R^{5a}$ is selected from the group consisting of hydrogen, halogen, hydrocarbyl, and substituted hydrocarbyl;

$R^6$ is selected from the group consisting of hydrogen, hydrocarbyl, and substituted hydrocarbyl;

$R^7$ and $R^8$ are independently selected from the group consisting of hydrogen, OH, $NH_2$, SH, hydrocarbyl, and substituted hydrocarbyl, wherein $R^8$ and $R^9$ together may form a group selected from the group consisting of =O and =S;

X is halogen;

Y is selected n is from the group consisting of alkyl, substituted alkyl, carbonyl, and alkyl carbonyl; and Z is selected from the group consisting of {—}O{—} and {—}NH{—}.

Other aspects and iterations of the invention are described in more detail below.

DETAILED DESCRIPTION OF THE INVENTION

The present invention provides processes and intermediate compounds for producing sinomenine derivatives. These sinomenine derivatives may be more specific, more efficacious, and/or more potent than sinomenine. Additionally, these sinomenine derivatives may have fewer side effects than sinomenine.

(I) Sinomenine Derivatives

The sinomenine derivatives and intermediates that may be used to make sinomenine derivatives generally comprise formula (I), (Ia), (Ib), and (Ic), as described below.

(a) Compounds Having Formula (I)

In one embodiment of the invention, the sinomenine derivative comprises formula (I):

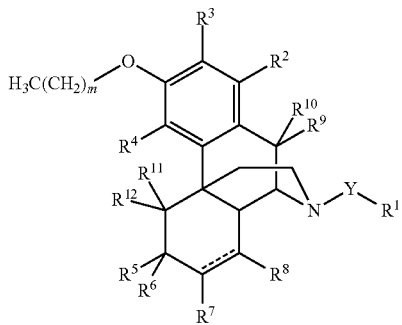

(I)

wherein:

$R^1$ is selected from the group consisting of hydrocarbyl and substituted hydrocarbyl;

$R^2$ and $R^3$ are independently selected from the group consisting of hydrogen, halogen, OH, $NH_2$, CN, hydrocarbyl, and substituted hydrocarbyl;

$R^4$ is selected from the group consisting of hydrogen, halogen, $NH_2$, CN, hydrocarbyl, substituted hydrocarbyl, and $OR^{4a}$;

$R^{4a}$ is selected from the group consisting of hydrogen and a bond that forms part of an ether-containing ring;

$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =$CHR^{5a}$, and —$O(CH_2)_2O$—;

$R^{5a}$ is selected from the group consisting of hydrogen, halogen, hydrocarbyl, and substituted hydrocarbyl;

$R^7$ is selected from the group consisting of hydrogen and $OR^{7a}$;

$R^{7a}$ is selected from the group consisting of hydrocarbyl and substituted hydrocarbyl;

$R^8$ is selected from the group consisting of hydrogen, hydrocarbyl, and substituted hydrocarbyl;

$R^9$ and $R^{10}$ are independently selected from the group consisting of hydrogen, OH, $NH_2$, SH, hydrocarbyl, and substituted hydrocarbyl, wherein $R^9$ and $R^{10}$ together may form a group selected from the group consisting of =O and =S;

$R^{11}$ and $R^{12}$ are independently selected from the group consisting of hydrogen, OH, halogen, hydrocarbyl, and substituted hydrocarbyl;

Y is selected from the group consisting of alkyl, substituted alkyl, carbonyl, and alkyl carbonyl;

m is an integer from 0 to 8; and

----- is a single bond or a double bond.

In another embodiment, the compound comprises Formula (I), wherein:

$R^1$ is selected from the group consisting of an alkyl group having from 1 to 8 carbon atoms, a vinyl group, an aryl group, cyclopropyl, cyclobutyl, {—}$CH(CF_3)_2$, {—}$CH(CH_3)CF_3$, {—}$CH$=$CF_2$ and {—}$CH_2CF_3$;

$R^2$ is selected from the group consisting of hydrogen and halogen;

$R^3$ is hydrogen;

$R^4$ is $OR^{4a}$;

$R^{4a}$ is selected from the group consisting of hydrogen and a bond that forms part of an ether-containing ring;

$R^5$ and $R^6$ are independently selected from the group consisting of hydrogen, OH, and $NH_2$, wherein $R^5$ and $R^6$ together may form =O;

$R^7$ is as defined above;

$R^8$, $R^9$, $R^{10}$, $R^{11}$ and $R^{12}$ are each hydrogen;

Y is selected from the group consisting of {—}$CH_2${—} and {—}$CO${—}; and m is 0.

In a preferred alternative of this embodiment, $R^7$ is $OR^{7a}$ and $R^{7a}$ is selected from the group consisting of alkyl and substituted alkyl having from 1 to 8 carbon atoms. In an exemplary iteration of this alternative, $R^{7a}$ is methyl.

In a further embodiment, the compound comprises Formula (I), wherein:

$R^1$ is cyclopropyl;

$R^2$ is halogen;

$R^3$ is hydrogen;

$R^4$ is $OR^{4a}$; $R^{4a}$ is selected from the group consisting of hydrogen and a bond that forms part of an ether-containing ring;

$R^5$ and $R^6$ are independently selected from the group consisting of hydrogen, OH, and $NH_2$, wherein $R^5$ and $R^6$ together may form =O;

$R^7$ is selected from the group consisting of hydrogen and $OR^{7a}$;

$R^{7a}$ is selected from the group consisting of alkyl and substituted alkyl having from 1 to 8 carbon atoms;

$R^8$, $R^9$, $R^{10}$, $R^{11}$, and $R^{12}$ are each hydrogen;

Y is selected from the group consisting of {—}$CH_2${—} and {—}$CO${—}; and m is 0.

For this embodiment, preferably, $R^2$ is bromide or chloride. In an exemplary alternative of this embodiment, $R^7$ is $OR^{7a}$ and $R^{7a}$ is methyl.

(b) Compounds Having Formula (Ia)

In a further embodiment of the invention, the compound comprises Formula (Ia):

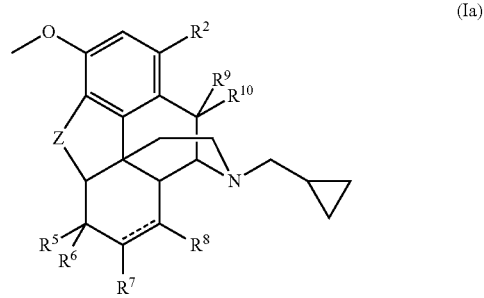

(Ia)

wherein:

$R^2$ is selected from the group consisting of hydrogen, halogen, OH, $NH_2$, CN, hydrocarbyl, and substituted hydrocarbyl;

$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =CHR$^{5a}$, and —O(CH$_2$)$_2$O—;

R$^{5a}$ is selected from the group consisting of hydrogen, halogen, hydrocarbyl, and substituted hydrocarbyl;

R$^7$ is selected from the group consisting of hydrogen and OR$^{7a}$;

R$^{7a}$ is selected from the group consisting of hydrocarbyl and substituted hydrocarbyl;

R$^8$ is selected from the group consisting of hydrogen, hydrocarbyl, and substituted hydrocarbyl;

R$^8$ and R$^{10}$ are independently selected from the group consisting of hydrogen, OH, NH$_2$, SH, hydrocarbyl, and substituted hydrocarbyl, wherein R$^9$ and R$^{10}$ together may form a group selected from the group consisting of =O and =S;

Z is selected from the group consisting of {—}O{—}, {—}S{—}, and {—}NH{—}; and

----- is a single bond or a double bond.

In an alternate embodiment, the compound comprises Formula (Ia), wherein:

R$^2$ is selected from the group consisting of halogen and hydrogen;

R$^5$ and R$^6$ are independently selected from the group consisting of hydrogen, OH, and NH$_2$ wherein R$^5$ and R$^6$ together may form =O;

R$^7$ is OR$^{7a}$ and R$^{7a}$ is selected from the group consisting of alkyl and substituted alkyl having from 1 to 8 carbon atoms;

R$^8$, R$^9$, and R$^{10}$ are each hydrogen; and

Z is oxygen.

In a preferred alternative of this embodiment, R$^2$ is halogen and R$^{7a}$ is methyl. Preferably, the halogen is bromide or chloride.

(c) Compounds Having Formula (Ib)

In still another embodiment, the compound comprises Formula (Ib):

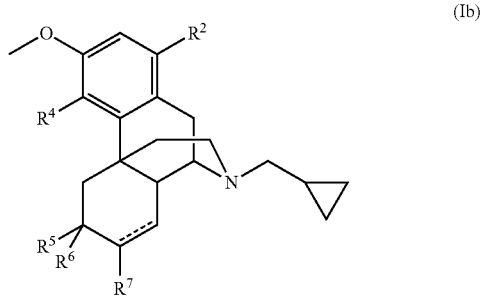

(Ib)

wherein:

R$^2$ is selected from the group consisting of hydrogen, halogen, OH, NH$_2$, CN, hydrocarbyl, and substituted hydrocarbyl;

R$^4$ is selected from the group consisting of hydrogen, halogen, NH$_2$, CN, hydrocarbyl, substituted hydrocarbyl, and OR$^{4a}$.

R$^{4a}$ is selected from the group consisting of hydrogen and a bond that forms part of an ether-containing ring;

R$^5$ and R$^6$ are independently selected from the group consisting of hydrogen, OH, NH$_2$, SH, hydrocarbyl, and substituted hydrocarbyl, wherein R$^5$ and R$^6$ together may form a group selected from the group consisting of =O, =NOH, =S, =CHR$^{5a}$, and —O(CH$_2$)$_2$O—;

R$^{5a}$ is selected from the group consisting of hydrogen, halogen, hydrocarbyl, and substituted hydrocarbyl;

R$^7$ is selected from the group consisting of hydrogen and OR$^{7a}$;

R$^{7a}$ is selected from the group consisting of hydrocarbyl and substituted hydrocarbyl; and ----- is a single bond or a double bond.

In another embodiment, the compound comprises Formula (Ib), wherein:

R$^2$ is selected from the group consisting of hydrogen and halogen;

R$^4$ is OR$^{4a}$;

R$^{4a}$ is selected from the group consisting of hydrogen and a bond that forms part of an ether-containing ring;

R$^5$ and R$^6$ are independently selected from the group consisting of hydrogen, OH, and NH$_2$ wherein R$^5$ and R$^6$ together may form =O; and R$^7$ is OR$^{7a}$ and R$^{7a}$ is selected from the group consisting of alkyl and substituted alkyl having from 1 to 8 carbon atoms.

In an exemplary alternative of this embodiment, R$^2$ is halogen and R$^{7a}$ is methyl. Preferably, the halogen is bromide or chloride.

(d) Compounds Having Formula (Ic)

In yet another embodiment, the compound comprises Formula (Ic):

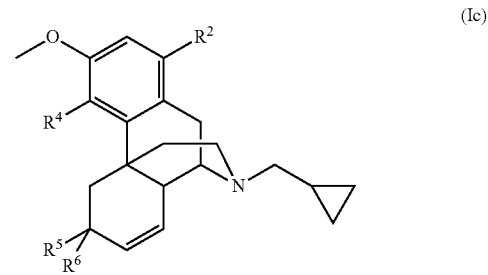

(Ic)

wherein:

R$^2$ is selected from the group consisting of hydrogen, halogen, OH, NH$_2$, CN, hydrocarbyl, and substituted hydrocarbyl;

R$^4$ is selected from the group consisting of hydrogen, halogen, NH$_2$, CN, hydrocarbyl, substituted hydrocarbyl, and OR$^{4a}$;

R$^{4a}$ is selected from the group consisting of hydrogen and a bond that forms part of an ether-containing ring;

R$^5$ and R$^6$ are independently selected from the group consisting of hydrogen, OH, NH$_2$, SH, hydrocarbyl, and substituted hydrocarbyl, wherein R$^5$ and R$^6$ together may form a group selected from the group consisting of =O, =NOH, =S, =CHR$^{5a}$, and —O(CH$_2$)$_2$O—; and R$^{5a}$ is selected from the group consisting of hydrogen, halogen, hydrocarbyl, and substituted hydrocarbyl.

In another alternate embodiment, the compound comprises Formula (Ic), wherein:

R$^2$ is selected from the group consisting of hydrogen and halogen;

R$^4$ is OR$^{4a}$;

R$^{4a}$ is selected from the group consisting of hydrogen and a bond that forms part of an ether-containing ring; and R$^5$ and R$^6$ are independently selected from the group consisting of hydrogen, OH, and NH$_2$, wherein R$^5$ and R$^6$ together may form =O.

In an exemplary iteration of this embodiment, R$^2$ is halogen. Preferably, the halogen is bromide or chloride.

(e) Exemplary Compounds

Non-limiting examples of exemplary compounds having formula (I), (Ia), (Ib), or (Ic) are presented in Table A.

TABLE A

| Compound No. | Structure |
|---|---|
| 8-1 | (structure) |
| 9-1 | (structure) |
| 10-1 | (structure) |
| 11-1 | (structure) |
| 12-1 | (structure) |

TABLE A-continued

| Compound No. | Structure |
|---|---|
| 13-1 | (structure) |

The compounds described above may have a (−) or (+) stereochemistry configuration, with respect to the rotation of polarized light. More specifically, each chiral center may have an R or an S configuration.

For ease of discussion, the ring atoms of the core morphinan structure referenced herein are numbered as follows:

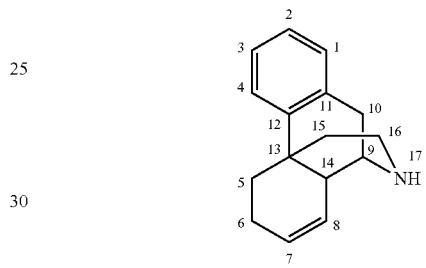

Carbons 13, 14, and 9 are chiral centers. Accordingly, the configuration of a compound of the invention having structure (I), (Ib), or (Ic) may be RRS, RSS, SRR, or SSR, with respect to C13, C14, and C9. Likewise, the configuration of compounds 8-1 and 9-1 may be RRS, RSS, SRR, or SSR, with respect to C13, C14, and C9. In exemplary embodiments, the configuration of compounds 8-1 and 9-1 may be (−)RSS.

In sinomenine derivatives in which an ether-containing ring links carbons 4 and 5, there are four chiral carbons, i.e., carbons 5, 13, 14, and 9. Thus, the configuration of compounds of the invention having formula (Ia) may be RRRS, RRSS, SRRS, SRSS, RSRR, RSSR, SSRR, or SSSR, with respect to C5, C13, C14, and C9. Likewise, the configuration of compounds 10-1, 11-1, 12-1, and 13-1 may be RRRS, RRSS, SRRS, SRSS, RSRR, RSSR, SSRR, or SSSR, with respect to C5, C13, C14, and C9. In exemplary embodiments, the configuration of compounds 10-1, 11-1, 12-1, and 13-1 may be (+)SRSS.

The invention also encompasses salts of any of the above-described compounds having Formula (I), (Ia), (Ib), and (Ic). Exemplary salts include without limitation hydrochloride, hydrobromide, phosphate, sulfate, methansulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

(II) Processes for Preparing Sinomenine Derivatives

Another aspect of the invention provides processes for preparing the sinomenine derivatives having Formula (I), (Ia), (Ib), and (Ic) or intermediates that may be used in the production of sinomenine derivatives. While it is envisioned that the synthetic routes described herein may be utilized to produce (+/−)-sinomenine derivatives, in an exemplary aspect of the invention, the process encompasses the production of (+)-sinomenine derivatives. For purposes of illustration, Reaction Scheme 1 depicts production of compound 7 in accordance with one aspect of the invention.

wherein:

$R^1$ is selected from the group consisting of hydrocarbyl and substituted hydrocarbyl;

$R^2$ and $R^3$ are independently selected from the group consisting of hydrogen, halogen, OH, $NH_2$, CN, hydrocarbyl, and substituted hydrocarbyl;

Reaction Scheme 1:

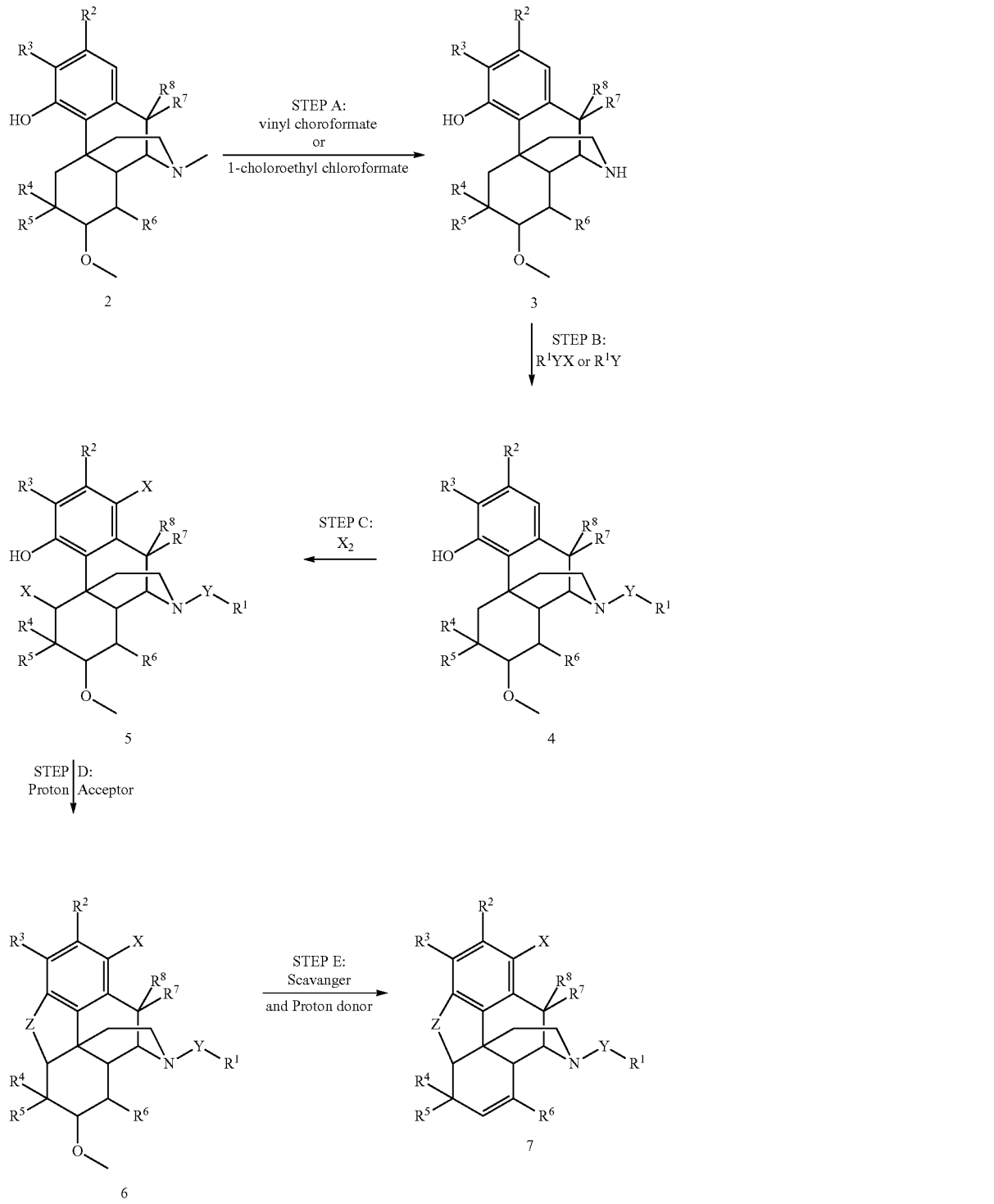

$R^4$ and $R^5$ are independently selected from the group consisting of hydrogen, OH, $NH_2$, CN, hydrocarbyl, and substituted hydrocarbyl; wherein $R^4$ and $R^5$ together may form a group selected from the group consisting of =O, =NOH, =S, =CHR$^{5a}$, and —O(CH$_2$)$_2$O—;

$R^{5a}$ is selected from the group consisting of hydrogen, halogen, hydrocarbyl, and substituted hydrocarbyl;

$R^6$ is selected from the group consisting of hydrogen, hydrocarbyl, and substituted hydrocarbyl;

$R^7$ and $R^8$ are independently selected from the group consisting of hydrogen, OH, $NH_2$, SH, hydrocarbyl, and substituted hydrocarbyl, wherein $R^7$ and $R^8$ together may form a group selected from the group consisting of =O and =S;

X is halogen;

Y is selected from the group consisting of alkyl, substituted alkyl, carbonyl, and alkyl carbonyl; and Z is selected from the group consisting of oxygen, nitrogen and sulfur.

In an alternative of this embodiment, the constituents of the reaction comprise:

$R^1$ is selected from the group consisting of an alkyl group having from 1 to 8 carbon atoms, a vinyl group, an aryl group, cyclopropyl, cyclobutyl, {—}CH(CF$_3$)$_2$, {—}CH(CH$_3$)CF$_3$, {—}CH=CF$_2$, and {—}CH$_2$CF$_3$, $R^2$ and $R^3$ are independently selected from the group consisting of hydrogen, halogen, OH, $NH_2$ CN, acyl, alkyl, alkenyl, aryl, alkoxyl, and alkylamino;

$R^4$ and $R^5$ are independently selected from the group consisting of hydrogen, OH, and alkoxyl, wherein $R^4$ and $R^5$ together may form a group selected from the group consisting of =O, =NOH, and —O(CH$_2$)$_2$O—;

$R^6$ is selected from the group consisting of hydrogen and alkyl;

$R^7$ and $R^8$ are independently selected from the group consisting of hydrogen, OH and $NH_2$, wherein $R^7$ and $R^8$ together may form =O;

X is selected from the group consisting of bromide and chloride;

Y is selected from the group consisting of {—}CH$_2${—} and {—}CO{—}; and

Z is oxygen.

In a further iteration of this alternative, $R^1$ is cyclopropyl; $R^2$ is hydrogen; $R^3$ is {—}O(CH$_2$)$_m$CH$_3$; $R^4$ and $R^5$ together form =O; $R^6$, $R^7$, and $R^8$ are each hydrogen; and m is from 0 to 8. In an exemplary iteration, X is bromide and m is 0.

(a) Step A: Conversion of Compound 2 to Compound 3

In Step A of the process, the substrate, compound 2, is contacted with either vinyl chloroformate or 1-chloroethyl chloroformate, followed by hydrolysis of the reaction mixture in the presence of either a dilute solution of a proton donor or a proton acceptor to form compound 3.

The reaction may be conducted in the presence of a solvent. The solvent may be an aprotic solvent. Non-limiting examples of aprotic solvents include ether solvents, acetone, acetonitrile, benzene, diethoxymethane, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethylacetamide (DMAC), N-methylpyrrolidinone (NMP), ethyl acetate, ethyl formate, ethyl methyl ketone, formamide, isobutylmethylketone, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), toluene, trichloromethane.

In a preferred embodiment, the aprotic solvent may be dimethylformamide, dimethyl sulfoxide, dioxane, formamide, or N-methylacetamide.

The weight ratio of aprotic solvent to compound 2 may range from about 1:1 to about 20:1. In one embodiment, the weight ratio of solvent to compound 2 may range from about 1:1 to about 3:1. In another embodiment, the weight ratio of solvent to compound 2 may range from about 6:1 to about 12:1. In still another embodiment, the weight ratio of solvent to compound 2 may range from about 12:1 to about 20:1. In a preferred embodiment, the weight ratio of solvent to compound 2 may range from about 3:1 to about 6:1.

The reaction mixture is typically then treated with a dilute solution of proton donor or proton acceptor to form compound 3. In general, the proton donor has a pKa less than about 6. Suitable proton donors include, but are not limited to, HOAc, HCO$_2$H, H$_2$CO$_3$, MeSO$_3$H, poly H$_3$PO$_4$, H$_3$PO$_4$, H$_2$SO$_4$, HCl, HBr, HI, CF$_3$SO$_3$H, and p-methyltoluenesulfonic acid. The proton acceptor typically has a pKa between about 7 and about 13. Suitable proton acceptors having this characteristic include borate salts (such as, for example, NaBO$_3$), di- and tri-basic phosphate salts (such as, for example, Na$_2$HPO$_4$ and Na$_3$PO$_4$, and the like), bicarbonate salts (such as, for example, NaHCO$_3$, KHCO$_3$, LiCO$_3$, and the like), carbonate salts (such as, for example, Na$_2$CO$_3$, K$_2$CO$_3$, Li$_2$CO$_3$, and the like), organic bases (such as, for example, pyridine, triethylamine, diisopropylethylamine, N-methylmorpholine, N,N-dimethylaminopyridine), and mixtures of any of the above. In a preferred embodiment, the proton acceptor may be NaHCO$_3$, KHCO$_3$, LiCO$_3$, Na$_2$CO$_3$, K$_2$CO$_3$, Li$_2$CO$_3$, or a mixture thereof. In an exemplary embodiment, the proton acceptor may be NaHCO$_3$.

The amount of the reactants contacted with compound 2 can and will vary. Typically, the weight ratio of compound 2 to vinyl chloroformate or 1-chloroethyl chloroformate to proton donor or proton acceptor may range from about 1:2:1 to about 1:20:20. In one embodiment, the weight ratio of compound 2 to vinyl chloroformate or 1-chloroethyl chloroformate to proton donor or proton acceptor may range from about 1:2:1 to about 1:4:4. In another embodiment, the weight ratio of compound 2 to vinyl chloroformate or 1-chloroethyl chloroformate to proton donor or proton acceptor may range from about 1:4:4 to about 1:10:10. In still another embodiment, the weight ratio of compound 2 to vinyl chloroformate or 1-chloroethyl chloroformate to proton donor or proton acceptor may range from about 1:10:10 to about 1:20:20. In a preferred embodiment, the weight ratio of compound 2 to vinyl chloroformate or 1-chloroethyl chloroformate to proton donor or proton acceptor may range from about 1:3:3 to about 1:12:12.

The reaction may be conducted at a temperature that ranges from about 50° C. to about 120° C. In one embodiment, the temperature of the reaction may range from about 100° C. to about 120° C. In an alternate embodiment, the temperature of the reaction may range from about 80° C. to about 100° C. In a preferred embodiment, the temperature of the reaction may range from about 50° C. to about 80° C. The reaction is preferably performed under ambient pressure, and preferably in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of compound 1 and a significantly increased amount of compound 2 compared to the amounts of each present at the beginning of the reaction.

The yield of compound 3 may vary. Typically, the yield of compound 3 may range from about 40% to about 70%. In one embodiment, the yield of compound 3 may range from about 40% to about 50%. In another embodiment, the yield of compound 3 may range from about 50% to about 60%. In still another embodiment, the yield of compound 3 may range from about 60% to about 70%.

(b) Step B: Conversion of Compound 3 to Compound 4

In Step B of the process, compound 3 is alkylated with $R^1YX$ or undergoes reductive amination with $R^1Y$ to form compound 4. $R^1$, Y, and X are as defined above. Preferably, Y is —$CH_2$— or —CHO. The process comprises contacting compound 3 with either $R^7YX$ or $R^7Y$ to form compound 4.

The reaction may be conducted in the presence of a solvent. The solvent may be an aprotic solvent. Suitable aprotic solvents are as described in Step A of the process. In general, the weight ratio of solvent to compound 3 may range from about 1:1 to about 20:1. In one embodiment, the weight ratio of solvent to compound 3 may range from about 1:1 to about 4:1. In an alternate embodiment, the weight ratio of solvent to compound 3 may range from about 4:1 to about 20:1.

The amount of $R^1YX$ or $R^1Y$ contacted with compound 3 may vary. In general, the weight ratio of compound 3 to $R^1YX$ or $R^1Y$ may range from about 1:1 to about 1:3. In one embodiment, the weight ratio of compound 3 to $R^1YX$ or $R^1Y$ may range from about 1:1 to about 1:2. In another embodiment, the weight ratio of compound 3 to $R^1YX$ or $R^1Y$ may range from about 1:2 to about 1:3. In a preferred embodiment, the weight ratio of compound 3 to $R^1YX$ or $R^1Y$ may range from about 1:1.1 to about 1:1.5.

The temperature of the reaction may range from about 20° C. to about 100° C. In one embodiment, the temperature of the reaction may range from about 20° C. to about 40° C. In another embodiment, the temperature of the reaction may range from about 40° C. to about 70° C. In still another embodiment, the temperature of the reaction may range from about 70° C. to about 100° C. The reaction is preferably performed under ambient pressure, and preferably in an inert atmosphere (e.g., nitrogen or argon).

The reaction is typically allowed to proceed for a sufficient period of time until the reaction is complete, as determined by a technique, such as chromatography, well known in the art. In general, the yield of compound 4 may range from about 60% to about 80%. In one embodiment, the yield of compound 4 may range from about 60% to about 70%. In another embodiment, the yield of compound 4 may range from about 70% to about 80%.

(c) Step C: Conversion of Compound 4 to Compound 5

In Step C of the process, compound 4 is contacted with $X_2$ to form compound 5. $X_2$ is as defined above.

The reaction may be conducted in the presence of a solvent. The solvent may be an organic solvent. Suitable organic solvents include, but are not limited to, alkane and substituted alkane solvents (including cycloalkanes), aromatic hydrocarbons, esters, ethers, ketones, combinations thereof, and the like. Specific organic solvents that may be employed, include, for example, acetonitrile, benzene, butyl acetate, t-butyl methylether, t-butyl methylketone, chlorobenzene, chloroform, chloromethane, cyclohexane, dichloromethane, dichloroethane, diethyl ether, ethyl acetate, fluorobenzene, heptane, hexanes, isobutylmethylketone, isopropyl acetate, methylethylketone, methyltetrahydrofuran, pentyl acetate, n-propyl acetate, tetrahydrofuran, toluene, combinations thereof, and the like. In a preferred embodiment, the organic solvent may be benzene, chloroform, diethyl ether, ethyl acetate, heptane, hexane, or toluene.

In general, the weight ratio of organic solvent to compound 4 may range from about 5:1 to about 50:1. In one embodiment, the weight ratio of organic solvent to compound 4 may range from about 5:1 to about 20:1. In another embodiment, the weight ratio of organic solvent to compound 4 may range from about 20:1 to about 50:1.

Generally speaking, about 2 molar equivalents of $X_2$ are contacted with compound 4. In one embodiment, the weight ratio of compound 4 to $X_2$ may range from about 1:2 to about 1:2.5. In a preferred embodiment, the weight ratio of compound 4 to $X_2$ may be about 1:2.1.

Optionally, in one embodiment, a base may be added to the reaction of Step C. Generally, the base is a liquid at the temperature at which the reaction is conducted. For example, triethylamine is one such suitable base. It is generally believed, without being bound by theory, that the addition of a base to Step C may neutralize the acid formed (e.g., hydrogen bromide when X is bromide) so that the acid is prevented from reacting with reactants or products. In a further optional embodiment, a halogen scavenger may be added. For example, when the halogen is bromine, a bromine scavenger such as 2,3-dimethyl-1,3-butadiene may be added.

The temperature of the reaction may range from about –30° C. to about 0° C., and more preferably from about –20° C. to about –5° C. In one embodiment, the temperature of the reaction may range from about –20° C. to about –10° C. In another embodiment, the temperature of the reaction may range from about –10° C. to about –5° C. The reaction is preferably performed under ambient pressure, and preferably in an inert atmosphere (e.g., nitrogen or argon).

The reaction is typically allowed to proceed for a sufficient period of time until the reaction is complete, as determined using standard techniques. The yield of compound 5 may vary, depending upon the reaction conditions. In general, the yield of compound 5 may range from about 20% to about 70%. In one embodiment, the yield of compound 5 may range from about 20% to about 40%. In an alternate embodiment, the yield of compound 5 may range from about 40% to about 60%. In another alternate embodiment, the yield of compound 5 may range from about 60% to about 70%.

(d) Step D: Conversion of Compound 5 to Compound 6

Step D of the process involves a ring closure reaction. The process comprises contacting compound 5 with a proton acceptor to form compound 6.

The reaction may be conducted in the presence of a solvent. The solvent may be an aprotic solvent, a protic solvent, or a mixture thereof. Suitable aprotic solvents are as described in Step A of the process. Non-limiting examples of suitable protic solvents include methanol, ethanol, isopropanol, n-propanol, isobutanol, t-butanol, n-butanol, formic acid, acetic acid, and water. In one embodiment, the solvent may be an aprotic solvent or a combination thereof. In another embodiment, the solvent may be a protic solvent or a combination thereof. In still another embodiment, the solvent may be a solvent system in that it comprises a combination of aprotic solvent(s) and protic solvent(s).

Typically, the weight ratio of solvent or solvent system to compound 5 may range from about 5:1 to about 50:1. In one embodiment, the weight ratio of solvent or solvent system to compound 5 may range from about 5:1 to about 20:1. In another embodiment, the weight ratio of solvent or solvent system to compound 5 may range from about 20:1 to about 50:1.

In general, the proton acceptor used in this step has a pKa greater than about 12. Non-limiting examples of suitable proton acceptors having this characteristic include hydroxides of alkali metals and alkaline earth metals (such as, for example, NaOH and Ca(OH)$_2$ and the like), as well as group 1 salts of carbanions, amides, and hydrides (such as, for example, butyl lithium, sodium amide (NaNH$_2$), sodium hydride (NaH), and the like). In a preferred embodiment, the proton acceptor may be NaOH, KOH, LiOH, Ca(OH)$_2$ or NaH. In an exemplary embodiment, the proton acceptor may be NaOH.

The amount of proton acceptor added to the reaction is generally enough to keep the pH of the reaction mixture about 13 or higher. Typically, the weight ratio of compound 5 to proton acceptor may range from about 1:1.5 to about 1:20. In one embodiment, the weight ratio of compound 5 to proton acceptor may range from about 1:1.5 to about 1:5. In another embodiment, the weight ratio of compound 5 to proton acceptor may range from about 1:5 to about 1:20.

The temperature of the reaction may range from about −30° C. to about 0° C., and more preferably from about −20° C. to about −5° C. In one embodiment, the temperature of the reaction may range from about −20° C. to about −10° C. In another embodiment, the temperature of the reaction may range from about −10° C. to about −5° C. The reaction is preferably performed under ambient pressure, and preferably in an inert atmosphere (e.g., nitrogen or argon).

The reaction is typically allowed to proceed for a sufficient period of time until the reaction is complete, as determined using techniques known to those of skill in the art. The yield of compound 6 made from compound 5 may vary, depending upon the reaction conditions. In general, the yield of compound 6 may range from about 70% to about 95%. In one embodiment, the yield of compound 6 may range from about 70% to about 80%. In another embodiment, the yield of compound 6 may range from about 80% to about 90%. In yet another embodiment, the yield of compound 6 may range from about 90% to about 95%.

(e) Step E: Conversion of Compound 6 to Compound 7

In Step E of the process, compound 6 is contacted with a scavenger and a proton donor to form compound 7.

The reaction may be conducted in the presence of a solvent. The solvent may be an aprotic solvent, as detailed above in Step A of the process. Typically, the weight ratio of solvent or solvent system to compound 6 may range from about 5:1 to about 50:1. In one embodiment, the weight ratio of solvent or solvent system to compound 6 may range from about 5:1 to about 20:1. In another embodiment, the weight ratio of solvent or solvent system to compound 6 may range from about 20:1 to about 50:1.

Typically, the scavenger is an alcohol scavenger. The alcohol may have from about one to about eight carbon atoms. In an exemplary embodiment, the alcohol scavenger is a methanol scavenger. Non-limiting examples of suitable alcohol scavengers include P$_2$O$_5$, POCl$_3$, POBr$_3$, PCl$_3$, SOCl$_2$, SOBr$_2$, MeSO$_2$Cl, (MeSO$_2$)$_2$O, SO$_3$, (CF$_3$SO$_2$)$_2$O, and (CF$_3$CO)$_2$O. In a preferred embodiment, the alcohol scavenger may be POCl$_3$.

The proton donor generally has a pKa less than about 0. Suitable proton donors having this characteristic include, but are not limited to, MeSO$_3$H, poly H$_3$PO$_4$, H$_3$PO$_4$, H$_2$SO$_4$, HCl, HBr, HClO$_4$, HI, HNO$_3$, CF$_3$SO$_3$H, p-methyltoluenesulfonic acid, HClO$_3$, HBrO$_4$, HIO$_3$, and HIO$_4$. In a preferred embodiment, the proton donor may be MeSO$_3$H, poly H$_3$PO$_4$, H$_3$PO$_4$, H$_2$SO$_4$, HCl, HBr, CF$_3$SO$_3$H, and p-methyltoluenesulfonic acid. In a preferred embodiment, the proton donor may be MeSO$_3$H.

In general, the weight ratio of compound 6 to scavenger to proton donor is from about 1:0.5:2 to about 1:2:20. In one embodiment, the weight ratio of compound 6 to scavenger to proton donor is from about 1:0.5:2 to about 1:1:5. In an alternate embodiment, the weight ratio of compound 6 to scavenger to proton donor is from about 1:1:5 to about 1:2:20.

The temperature of the reaction may range from about 0° C. to about 100° C., and more preferably from about 20° C. to about 45° C. In one embodiment, the temperature of the reaction may range from about 20° C. to about 35° C. In another embodiment, the temperature of the reaction may range from about 35° C. to about 45° C. The reaction is preferably performed under ambient pressure, and preferably in an inert atmosphere (e.g., nitrogen or argon).

The reaction is typically allowed to proceed for a sufficient period of time until the reaction is complete, as determined using standard techniques. The yield of compound 7 generally will range from about 20% to about 60%. In one embodiment, the yield of compound 7 may range from about 20% to about 40%. In another embodiment, the yield of compound 7 may range from about 40% to about 50%. In yet another embodiment, the yield of compound 7 may range from about 50% to about 60%.

(f) Preparation of Exemplary Compounds

Compound 7 and certain intermediate compounds, such as compounds 4 and 6, depicted in Reaction Scheme 1 may be utilized to prepare one or more sinomenine derivative compounds having formula (I), (Ia), (Ib), or (Ic). By way of non-limiting example, compounds 4, 6, and 7 may be reduced to form compounds 8-1, 10-1, and 13-1, respectively. A variety of reducing approaches may be employed including, for example, chemical reduction, catalytic reduction, and the like. Representative reducing agents for use in chemical reduction include hydrides (e.g., hydrogen iodide, hydrogen sulfide, lithium aluminum hydride, sodium borohydride, sodium cyanoborohydride, and the like), or combinations of a metal (e.g., tin, zinc, or iron) or a metal compound (e.g., chromium chloride, chromium acetate, and the like) with an organic or inorganic acid (e.g., formic acid, acetic acid, propionic acid, trifluoroacetic acid, p-toluenesulfonic acid, hydrochloric acid, and the like), samarium iodide, and others. In an exemplary embodiment, the reducing agent may be sodium borohydride (NaBH$_4$). Representative reducing agents for use in catalytic reduction methods with hydrogen include commonly used catalysts such as, for example, platinum catalysts (e.g., platinum black, colloidal platinum, platinum oxide, platinum plate, platinum sponge, platinum wire, and the like), palladium catalysts (e.g., palladium black, palladium on barium carbonate, palladium on barium sulfate, colloidal palladium, palladium on carbon, palladium hydroxide on carbon, palladium oxide, palladium sponge, and the like), nickel catalysts (e.g., nickel oxide, Raney nickel, reduced nickel, and the like), cobalt catalysts (e.g., Raney cobalt, reduced cobalt, and the like), iron catalysts (e.g., Raney iron, reduced iron, Ullmann iron, and the like), and others. For the preparation of compounds 8-1 and 10-1, a combination of chemical and catalytic reduction may be required.

Furthermore, compounds 4-1 and 6-1 (see Reaction Scheme 2 in the Examples) may undergo reductive amination to form compounds 9-1 and 11-1, respectively. Suitable reagents and conditions are generally known in the art. As an example, reductive amination may be conducted in the presence of hydrogen gas with a palladium, platinum, or nickel catalysts, as defined above. Alternatively, the reductive amination may comprise hydrogen and a Noyori catalyst, formic acid, and a tertiary amine.

Additionally, compound 7-1 (see Reaction Scheme 2 in the Examples) may undergo hydrogenation to form compound 12-1. The hydrogenation may be catalytic, that is in the presence of hydrogen and a metal catalyst, as detailed above.

Suitable metal catalysts include platinum, palladium, rhodium, ruthenium, and the like. One of skill in the art will be familiar with reaction conditions and other variables.

DEFINITIONS

The term "acyl," as used herein alone or as part of another group, denotes the moiety formed by removal of the hydroxy group from the group COOH of an organic carboxylic acid, e.g., RC(O)—, wherein R is $R_1$, $R_1O$—, $R_1R_2N$—, or $R_1S$—, $R_1$ is hydrocarbyl, heterosubstituted hydrocarbyl, or heterocyclo, and $R_2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alcohol scavenger" as used herein is a reagent that can react with an alcohol and release an acid at the same time.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl, and the like.

The term "alkaryl" or "alkylaryl" as used herein describes groups which are preferably aryl groups having a lower alkyl substituent, such as toluoyl, ethylphenyl, or methylnapthyl.

The term "alkenyl" as used herein describes groups which are preferably lower alkenyl containing from two to eight carbon atoms in the principal chain and up to 20 carbon atoms. The may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aralkyl" as used herein describes groups which are preferably lower alkyl containing from one to eight carbon atoms having an aryl substituent, such as benzyl, phenylethyl, or 2-naptheylmethyl.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denotes optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters, and ethers.

The term "heteroaryl" as used herein alone or as part of another group denotes optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters, and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters, and ethers.

The term "hydroxy protecting group" as used herein denotes a group capable of protecting a free hydroxy group ("protected hydroxy"), which, subsequent to the reaction for which protection is employed, may be removed without disturbing the remainder of the molecule.

When introducing elements of the present invention or the preferred embodiments thereof, the articles "a", "an", "the" and "said" are intended to mean that there are one or more of the elements. The terms "comprising," "including," and "having" are intended to be inclusive and mean that there may be additional elements other than the listed elements.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate various iterations of the invention.

Example 1

Preparation of Sinomenine Derivatives

A synthetic route for preparing derivatives of sinomenine is presented below in Reaction Scheme 2.

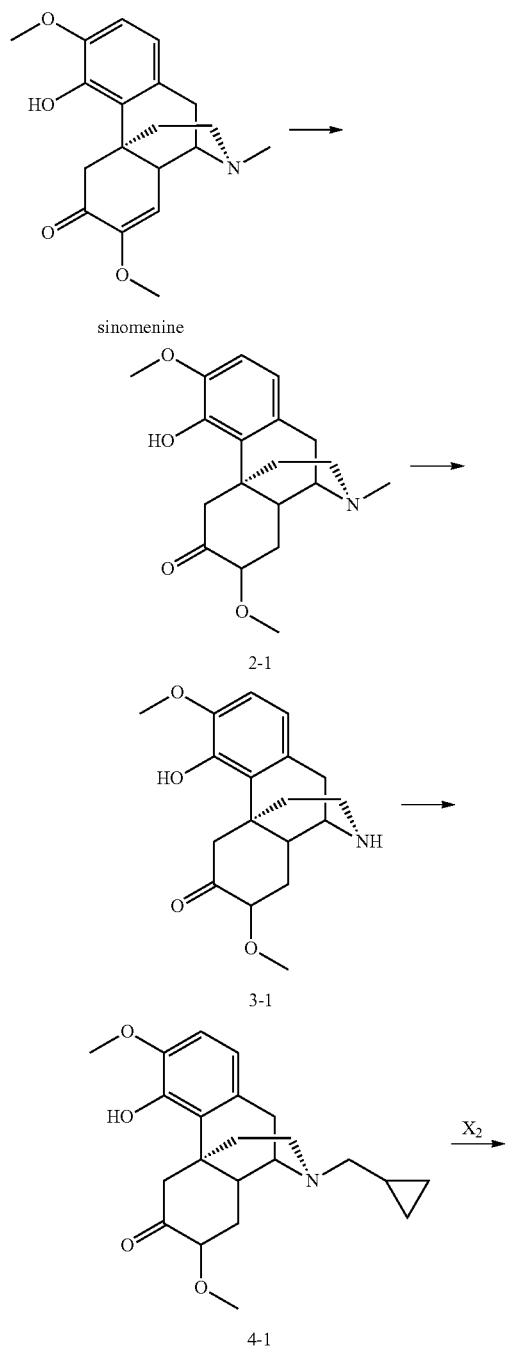

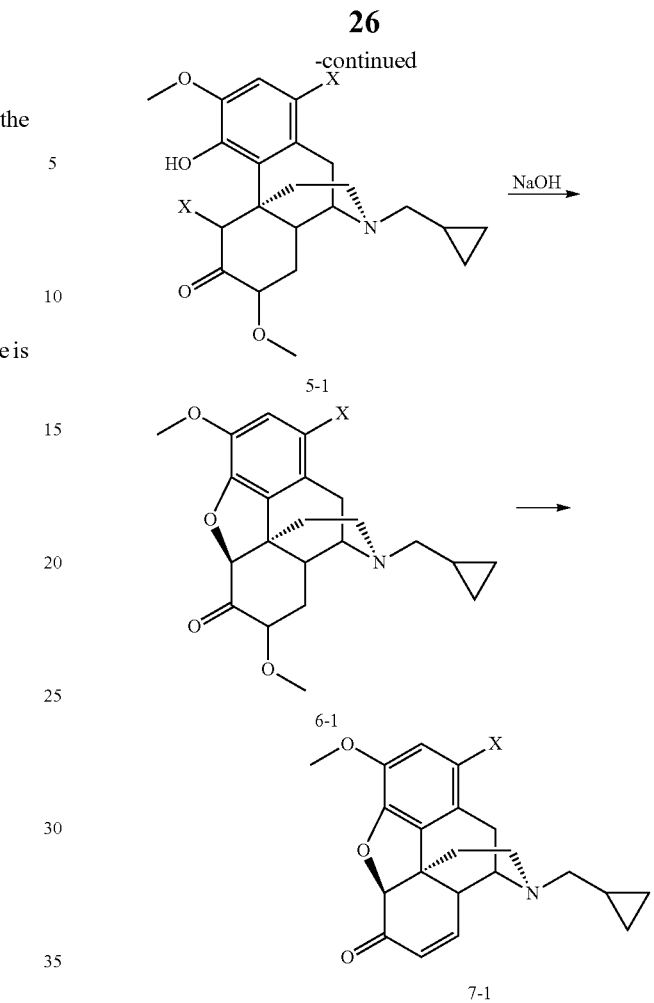

Sinomenine may be converted to compound 2-1 by catalytic hydrogenation. That is, sinomenine may be contacted with $H_2$, Pd/C, at a high temperature. Compound 2-1 may be contacted with either vinyl chloroformate or 1-chloroethyl chloroformate in the presence of an aprotic solvent, and then hydrolyzed in a dilute solution of a weak acid or weak base, such as $NaHCO_3$, to form compound 3-1. Compound 3-1 may be alkylated with cyclopropylCH$_2$X (wherein X is a halogen) or may undergo reductive amination with cyclopropylCHO to form compound 4-1. Compound 4-1 may be reacted with two equivalences of X to form compound 5-1. A strong base (i.e., having a pKa>13), such as NaOH, may be added to the previous reactive mixture to form compound 6-1. Compound 6-1 may be reacted with an alcohol scavenger, such as $POCl_3$, and a strong acid (i.e., having a pKa<0) to form compound 7-1.

Example 2

Bromination with TEA Addition

The addition of a base, such as triethylamine, that is liquid at low temperatures, to the bromination reaction at low temperatures, prior to the aqueous sodium hydroxide quench, neutralizes the HBr produced in the reaction. This prevents this acid from reacting with the product as the reaction solution is warmed to temperatures at which it can be mixed with aqueous sodium hydroxide. In one example, TEA may be added to the following bromination Reaction 3:

Reaction Scheme 3:

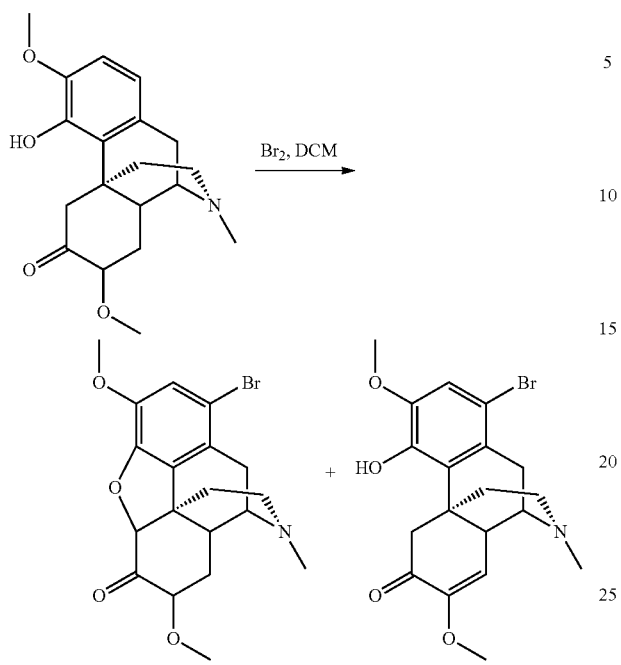

3.0 g of Dihydrosinomenine were dissolved in 150 mL dichloromethane in a 500 mL 3-neck flask. 0.12 mL meslic acid were added. The solution was cooled to −30° C. A solution of 1.02 mL Br₂ in 10 mL dichloromethane was slowly added. For the first half of the bromine addition, the bromine color disappeared rapidly. The solution was allowed to warm to −20° C. and the reaction was monitored by HPLC. When the peak for the mono-bromo intermediate had finished decreasing, 3.79 mL of Triethylamine were added. The solution turned bright purple. The solution was then allowed to warm to 0° C. 54.3 mL of 1N Aq. NaOH were added. The reaction mixture was transferred to a separation funnel. The two phases were separated and the aqueous phase was extracted with dichloromethane twice more. The organic layers were combined, dried with magnesium sulfate, and stripped to a yellow solid (3.55 g) containing 14 area % Cmp. 2 and 44 area % Cmp. 3. The structures for Cmp. 2 and Cmp. 3 are supported by mass spectrometry and NMR data.

Example 3

Bromination with TEA Addition and 2,3-dimethyl-1,3-butadiene Addition

The addition of a bromine scavenger, such as 2,3-dimethyl-1,3-butadiene, to the reaction illustrated in Reaction Scheme 3 before the aqueous sodium hydroxide quench removes excess bromine. This prevents the excess bromine from oxidizing the phenoxide compounds, formed when the aqueous sodium hydroxide is added, thus preventing the formation of highly colored impurities.

3.0 g of Dihydrosinomenine were dissolved in 150 mL dichloromethane in a 500 mL 3-neck flask. 0.12 mL meslic acid were added. The solution was cooled to −30° C. A solution of 1.02 mL Br₂ in 10 mL dichloromethane was slowly added. For the first half of the bromine addition, the bromine color disappeared rapidly. The solution was allowed to warm to −20° C. and the reaction was monitored by HPLC. When the peak for the mono-bromo intermediate had finished decreasing, 2.78 mL of Triethylamine were added. The solution turned bright purple. Then 0.31 mL of 2,3-dimethyl-1,3-butadiene were added. The color of the solution lightened to brownish dark green. The solution was then allowed to warm to 0° C. 54.3 mL of 1N Aq. NaOH were added. The reaction mixture was transferred to a separation funnel. The two phases were separated and the aqueous phase was extracted with dichloromethane twice more. The organic layers were combined, dried with magnesium sulfate, and stripped to a yellow solid (3.39 g).

Example 4

Enrichment of Cmp. 2 by Extraction of Cmp. 3

Cmp. 2 and Cmp. 3 may be separated by extraction of a solution in an organic solvent, such as toluene or a mixture of toluene and hexanes, with a basic aqueous solution. For example, 1.00 g of the product from the "Bromination with TEA addition and 2,3-dimethyl-1,3-butadiene addition" example was dissolved in 150 mL toluene. This solution was then extracted with a solution of 50 mL concentrated ammonium hydroxide and 50 mL water. The toluene layer was then extracted with a solution of 25 mL concentrated ammonium hydroxide and 75 mL water. The toluene layer was then extracted with a solution of 15 mL concentrated ammonium hydroxide and 85 mL water. The three aqueous extraction layers were combined. HPLC analysis showed the preferential extraction of Cmp. 3 into the aqueous layers. The toluene layer was again extracted three times as above. HPLC analysis showed only negligible amounts of Cmp. 3 in the aqueous layers. 20 mL of toluene were stripped under vacuum from the toluene layer. 50 mL of hexanes were added. This organic solution was extracted as above. HPLC analysis showed the preferential extraction of Cmp. 3 into the aqueous layers. The organic layer was dried with magnesium sulfate and stripped to 0.35 g of a brown oil containing 23 area % Cmp. 2 and 15 area % Cmp. 3. The aqueous layers from the first and third series of extractions were combined. Excess amounts of ammonia were stripped off under vacuum. The aqueous solution was then extracted three times with dichloromethane. The dichloromethane layers were combined, dried with magnesium sulfate, and stripped to 0.23 g of gummy solids containing mostly Cmp. 3.

Example 5

Preparation of 1-Bromo-Dihydrosinomenine

Dihydrosinomenine may be mono-brominated to 1-bromo-dihydrosinomenine (Cmp. 4) according to Reaction Scheme 4:

Reaction Scheme 4:

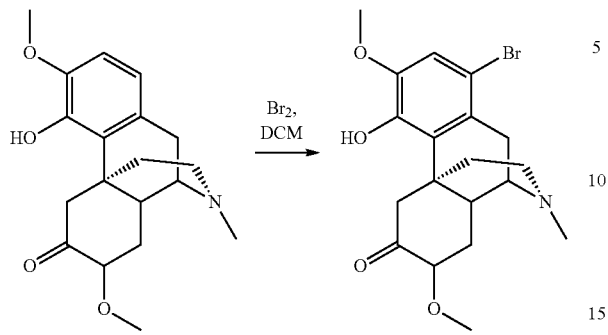

3.0 g of Dihydrosinomenine were dissolved in 150 mL dichloromethane in a 500 mL 3-neck flask. 0.12 mL meslic acid were added. The solution was cooled to −30° C. A solution of 0.44 mL Br$_2$ in 10 mL dichloromethane was slowly added. The bromine color disappeared rapidly. The solution was allowed to warm to −20° C. and the reaction was stirred for 15 minutes. The solution was then allowed to warm to 0° C. 10.4 mL of 1N Aq. NaOH were added. The reaction mixture was transferred to a separation funnel. The two phases were separated and the aqueous phase was extracted with dichloromethane twice more. The organic layers were combined, dried with magnesium sulfate, and stripped to a yellow solid (3.29 g) containing 90 area % Cmp. 4. The structure for Cmp. 4 is supported by mass spectrometry and NMR data.

Example 6

Preparation of 1-Bromo-7-Methoxylcodone

The compound may be prepared according to Reaction Scheme 5:

Reaction Scheme 5:

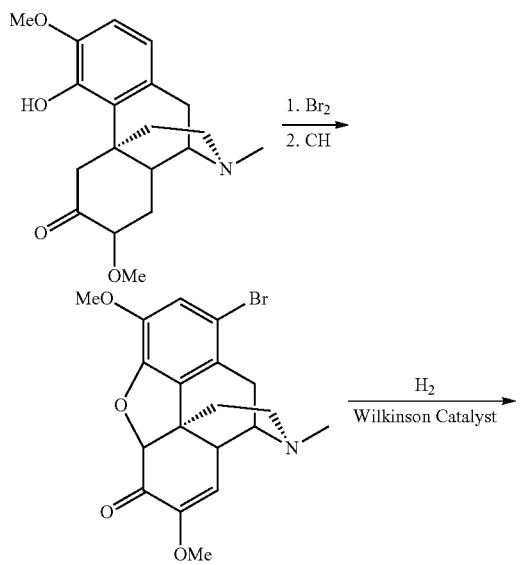

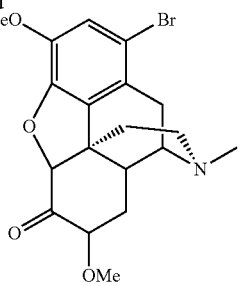

The solution of dihydrosinominene (1.0 g, 3.02 mmol, 1.0 eqv) in 30 mL acetonitrile was cooled to ∼−20° C. for 10 min. To the cooled solution was added methanesulfonic acid (1.1 mL, 17 mmol, 5.6 eqv). The reaction mixture turned clear solution. After stirring the reaction at −20° C. for five minutes, a solution of bromine (0.65 mL, 12.7 mmol, 4.2 eqv) in 6 mL acetonitrile was added dropwise. The reaction turned light brown solution. When the bath temperature was gradually raised to 0° C., the bath was switched to ice bath and kept the reaction stirring in ice bath for one hr; then the reaction was quenched by adding 1.2 g powder KOH; the reaction was gradually warmed to room temperature overnight. The reaction mixture was filtered, the solid was washed with acetonitrile (3×20 mL); the filtrate and washings were combined and evaporated; the residue was dissolved in a mixture of 30 mL 1.0 N NaOH and 150 ml of 1:9 DCM/EtOAc, the organic phase was washed with 1.0 N NaOH (5×40 mL), followed by washing with sodium metasulfate solution once, dried over anhydrous magnesium sulfate. After removing the volatiles, it gave an off white solid, 0.55 g, purity=84%, yield=45%. LC-MS: M+1=406.10.

Example 7

Synthesis of 1-Bromo-7-Methoxylcodone 2

With reference to Reaction Scheme 5, the solution of dihydrosinominene (5.0 g, 15 mmol, 1.0 eqv) in 150 mL acetonitrile was cooled to ∼-1-20° C. for 10 min. To the cooled solution was added methanesulfonic acid (5.5 mL, 84.8 mmol, 5.7 eqv). The reaction mixture turned clear solution. After stirring the reaction at −20° C. for five minutes, a solution of bromine (2.5 mL, 48.6 mmol, 3.2 eqv) in 30 mL acetonitrile was added dropwise. The reaction turned light brown solution. When the bath temperature was gradually raised to 0° C., the bath was switched to ice bath and kept the reaction stirring in ice bath for one hr; then the reaction was quenched by adding 6 g powder KOH; the reaction became solidified as a white chunk solid; to the reaction was added 200 mL acetonitrile. The resulting mixture was filtered and the solid was washed with acetonitrile (3×30 mL); the filtrate and washings were combined and evaporated to an oil. The oil residue was dissolved in 120 mL of ethyl acetate; the resulting solution was washed with 1N NaOH solution (5×80 mL) and dried over anhydrous magnesium sulfate. After removing the volatiles, it gave 2.3 g white solid, yield=38% with purity=85%.

Example 8

Synthesis of 1-Bromo-7-Methoxylhydrocodone 3

With reference to Reaction Scheme 5, dissolving 200 mg 1-bromo-7-methoxycodone in 10 mL of KH$_2$PO$_4$/K$_2$HPO$_4$ buffer with pH=7. The resulting solution was hydrogenised under 60 psi Hydrogen in the presence of Wilkinson Catalyst at 35° C. overnight. After cooling to room temperature, the volatiles were removed. It gave a brown mixture containing the desired product. LC-MS: M+1=408.14.

What is claimed is:

1. A compound having Formula (I):

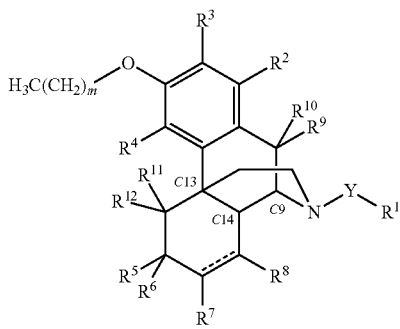

wherein:
$R^1$ is selected from the group consisting of hydrocarbyl and substituted hydrocarbyl;
$R^2$ is halogen;
$R^3$ is selected from the group consisting of hydrogen, halogen, OH, $NH_2$, CN, hydrocarbyl, and substituted hydrocarbyl;
$R^4$ is $OR^{4a}$;
$R^{4a}$ is a bond that forms park of an ether-containing ring;
$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =$CHR^{5a}$, and —$O(CH_2)_2O$—;
$R^{5a}$ is selected from the group consisting of hydrogen, halogen, hydrocarbyl, and substituted hydrocarbyl;
$R^7$ is $OR^{7a}$;
$R^{7a}$ is selected from the group consisting of hydrocarbyl and substituted hydrocarbyl;
$R^8$ is selected from the group consisting of hydrogen, hydrocarbyl, and substituted hydrocarbyl;
$R^9$ and $R^{10}$ are independently selected from the group consisting of hydrogen, OH, $NH_2$, SH, hydrocarbyl, and substituted hydrocarbyl, wherein $R^9$ and $R^{10}$ together may form a group selected from the group consisting of =O and =S;
$R^{11}$ and $R^{12}$ are independently selected from the group consisting of hydrogen, OH, halogen, hydrocarbyl, and substituted hydrocarbyl;
Y is selected from the group consisting of alkyl, substituted alkyl, carbonyl, and alkyl carbonyl;
m is an integer from 0 to 8; and
----- is a single bond or a double bond,
and further wherein C9, C13 and C14 reference carbon numbers 9, 13 and 14, respectively, of Formula (I).

2. The compound of claim 1, wherein:
$R^1$ is selected from the group consisting of an alkyl group having from 1 to 8 carbon atoms, a vinyl group, an aryl group, cyclopropyl, cyclobutyl, {—}$CH(CF_3)_2$, {—}$CH(CH_3)CF_3$, {—}$CH=CF_2$, and {—}$CH_2CF_3$;
$R^2$ is halogen;

$R^5$ and $R^6$ are independently selected from the group consisting of hydrogen, OH, and $NH_2$, wherein $R^5$ and $R^6$ together may form =O;
$R^3$ and $R^8$-$R^{12}$ are each hydrogen;
Y is selected from the group consisting of {—}$CH_2${—} and {—}CO{—}; and
m is 0.

3. The compound of claim 1, wherein the compound has Formula (Ia):

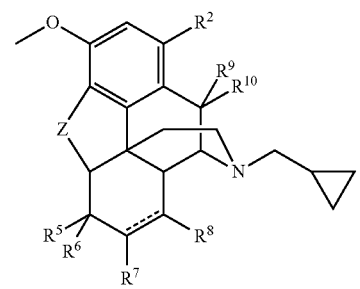

wherein:
$R^2$ is halogen;
$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =$CHR^{5a}$, and —$O(CH_2)_2O$—;
$R^{5a}$ is selected from the group consisting of hydrogen, halogen, hydrocarbyl, and substituted hydrocarbyl;
$R^7$ is $OR^{7a}$;
$R^{7a}$ is selected from the group consisting of hydrocarbyl and substituted hydrocarbyl;
$R^8$ is selected from the group consisting of hydrogen, hydrocarbyl, and substituted hydrocarbyl;
$R^9$ and $R^{10}$ are independently selected from the group consisting of hydrogen, OH, $NH_2$, SH, hydrocarbyl, and substituted hydrocarbyl, wherein $R^9$ and $R^{10}$ together may form a group selected from the group consisting of =O and =S;
Z is {—}O{—}; and
----- is a single bond or a double bond.

4. The compound of claim 1, wherein the compound has Formula (Ib):

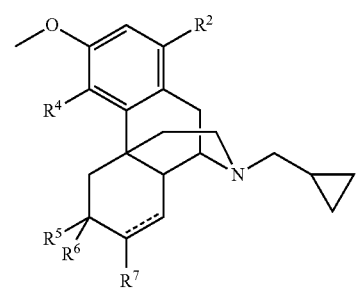

wherein:
$R^2$ is halogen;
$R^4$ is $OR^{4a}$;
$R^{4a}$ is a bond that forms part of an ether-containing ring;

$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =CHR$^{5a}$, and —O(CH$_2$)$_2$O—;

$R^{5a}$ is selected from the group consisting of hydrogen, halogen, hydrocarbyl, and substituted hydrocarbyl;

$R^7$ is $OR^{7a}$;

$R^{7a}$ is selected from the group consisting of hydrocarbyl and substituted hydrocarbyl; and ----- is a single bond or a double bond.

5. The compound of claim 1, wherein the compound is selected from the group consisting of:

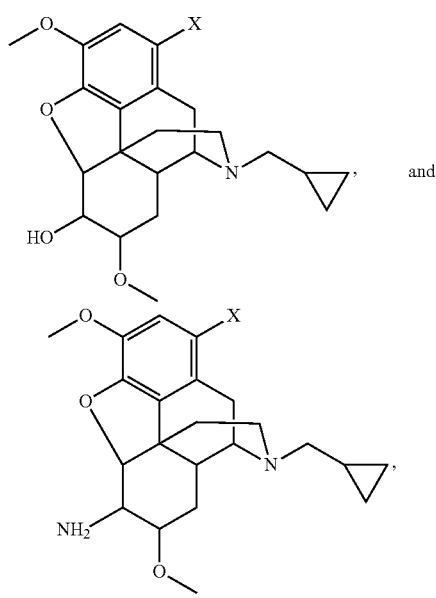

wherein X is halogen.

6. The compound of claim 1, wherein the optical activity of the compound is (−) or (+) and the configuration of C13, C14, and C9, respectively, is selected from the group consisting of RRS, RSS, SRR, and SSR.

7. A process for preparing a compound of Formula (I) of claim 1, the process comprising contacting a compound having Formula 5a with a proton acceptor to form a compound of Formula (I) according to the reaction scheme:

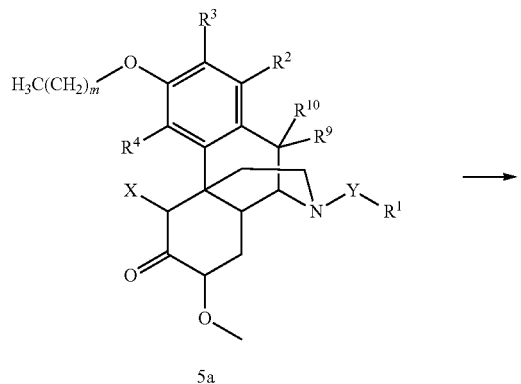

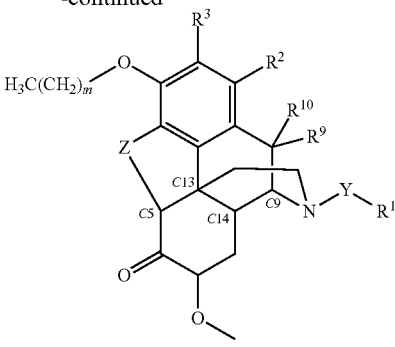

wherein
$R^1$ is selected from the group consisting of hydrocarbyl and substituted hydrocarbyl;
$R^2$ is halogen;
$R^3$ is selected from the group consisting of hydrogen, halogen, OH, $NH_2$, CN, hydrocarbyl, and substituted hydrocarbyl;
$R^4$ is OH;
$R^9$ and $R^{10}$ are independently selected from the group consisting of hydrogen, OH, $NH_2$, SH, hydrocarbyl, and substituted hydrocarbyl, wherein $R^9$ and $R^{10}$ together may form a group selected from the group consisting of =O and =S; and
X is halogen;
Y is selected from the group consisting of alkyl, substituted alkyl, carbonyl, and alkyl carbonyl;
m is an integer from 0 to 8; and
Z is {—}O{—},
and further wherein C5, C9, C13 and C14 reference carbon numbers 5, 9, 13 and 14, respectively, of the compound of Formula (I).

8. The process of claim 7, wherein the reaction is conducted in the presence of an aprotic solvent; the weight ratio of solvent to compound 5a is from about 5:1 to about 50:1; the proton acceptor has a pKa greater than about 13; the weight ratio of compound 5a to proton acceptor is from about 1:1.5 to about 1:20; the reaction is conducted at a temperature ranging from about −30° C. to about 0° C.; and the optical activity of compounds 5a and (I) is (−) or (+), and the configuration of C5, C13, C14, and C9, respectively, is selected from the group consisting of RRRS, RRSS, SRRS, SRSS, RSRR, RSSR, SSRR, and SSSR.

9. A compound having Formula (Ic):

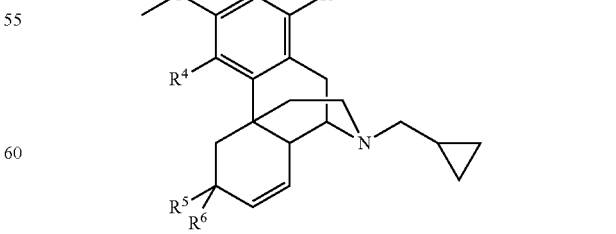

wherein:
$R^2$ is halogen;
$R^4$ is $OR^{4a}$;

$R^{4a}$ is a bond that forms part of an ether-containing ring;

$R^5$ and $R^6$ are independently selected from the group consisting of hydrogen, OH, $NH_2$, SH, hydrocarbyl, and substituted hydrocarbyl, wherein $R^5$ and $R^6$ together may form a group selected from the group consisting of =O, =NOH, =S, =CHR$^{5a}$, and —O(CH$_2$)$_2$O—; and $R^{5a}$ is selected from the group consisting of hydrogen, halogen, hydrocarbyl, and substituted hydrocarbyl.

10. A process for preparing a compound of Formula (Ic) of claim 9, the process comprising contacting a compound having Formula 6a with a scavenger and a proton donor to form the compound of Formula (Ic) according to the reaction scheme:

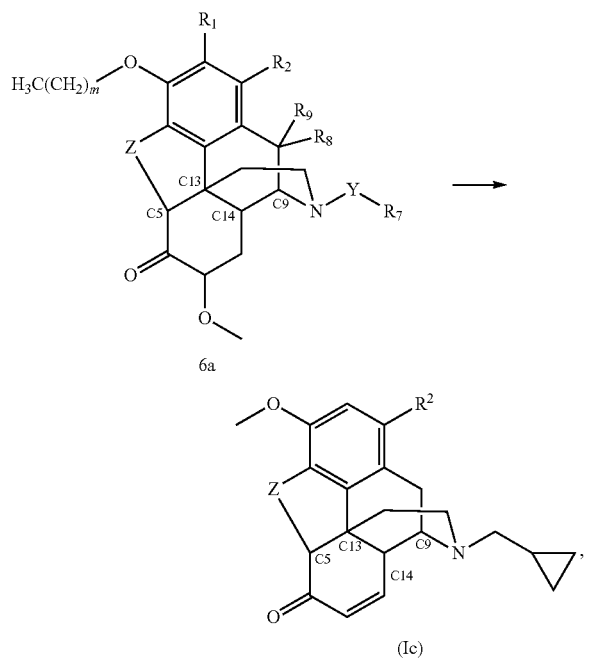

wherein $R^1$ is selected from the group consisting of hydrogen, halogen, OH, $NH_2$, CN, hydrocarbyl, and substituted hydrocarbyl;

$R^2$ is halogen;

$R^7$ is selected from the group consisting of hydrocarbyl and substituted hydrocarbyl;

$R^8$ and $R^9$ are independently selected from the group consisting of hydrogen, OH, $NH_2$, SH, hydrocarbyl, and substituted hydrocarbyl, wherein $R^8$ and $R^9$ together may form a group selected from the group consisting of =O and =S;

Y is selected from the group consisting of alkyl, substituted alkyl, carbonyl, and alkyl carbonyl;

m is an integer from 0 to 8; and

Z is {—}O{—}, and further wherein C5, C9, C13 and C14 reference carbon numbers 5, 9, 13 and 14, respectively, of the compounds of Formulas 6 and (Ic).

11. The process of claim 10, wherein the reaction is conducted in the presence of an aprotic solvent; the weight ratio of solvent to compound 6a is from about 5:1 to about 50:1; the scavenger is an alcohol scavenger; the proton donor has a pKa less than about 0; the weight ratio of compound 6a to scavenger to proton donor is from about 1:0.5:2 to about 1:2:20; the reaction is conducted at a temperature ranging from about 0° C. to about 100° C.; and the optical activity of compounds 6a and (Ic) is (−) or (+), and the configuration of C5, C13, C14, and C9, respectively, is selected from the group consisting of RRRS, RRSS, SRRS, SRSS, RSRR, RSSR, SSRR, and SSSR.

12. A process for preparation of a compound of Formula (Ic) of claim 9 according to the following reaction scheme:

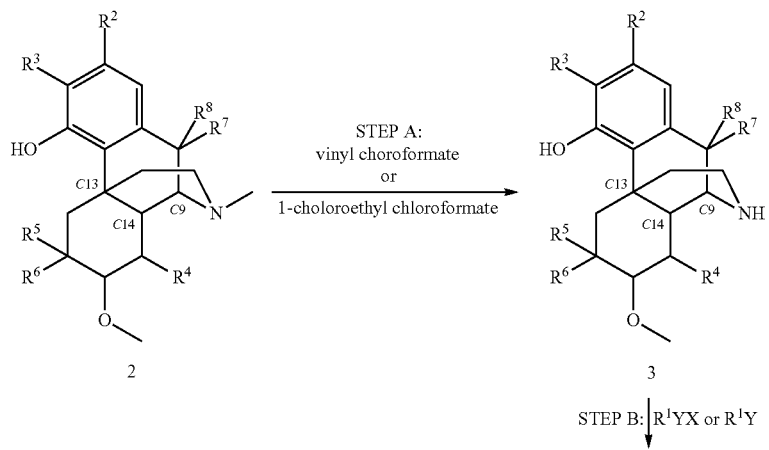

-continued

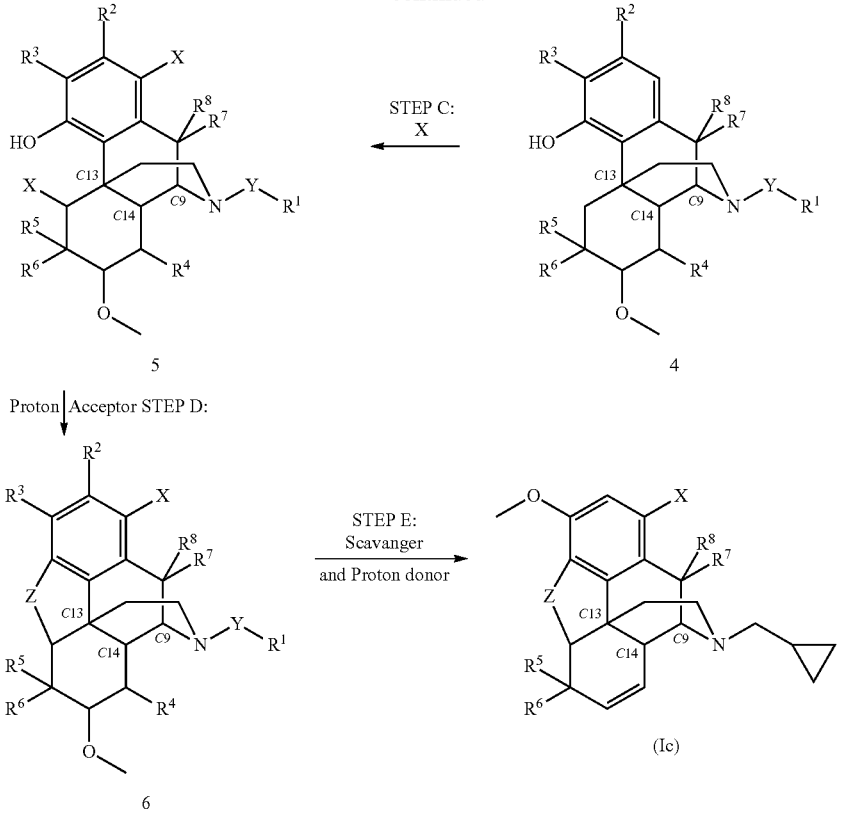

wherein:
R[1] is selected from the group consisting of hydrocarbyl and substituted hydrocarbyl;
R[2] and R[3] are independently selected from the group consisting of hydrogen, halogen, OH, NH$_2$, CN, hydrocarbyl, and substituted hydrocarbyl;
R[4] is selected from the group consisting of hydrogen, hydrocarbyl, and substituted hydrocarbyl;
R[5] and R[6] are independently selected from the group consisting of hydrogen, OH, NH$_2$, SH, hydrocarbyl, and substituted hydrocarbyl, wherein R[5] and R[6] together may form a group selected from the group consisting of =O, =NOH, =S, =CHR[5a], and —O(CH$_2$)$_2$O—;
R[5a] is selected from the group consisting of hydrogen, halogen, hydrocarbyl, and substituted hydrocarbyl;
R[7] and R[8] are independently selected from the group consisting of hydrogen, OH, NH$_2$, SH, hydrocarbyl, and substituted hydrocarbyl, wherein R[7] and R[8] together may form a group selected from the group consisting of =O and =S;
X is halogen;
Y is selected from the group consisting of alkyl, substituted alkyl, carbonyl, and alkyl carbonyl; and
Z is {—}O{—},
and further wherein C9, C13 and C14 reference carbon numbers 9, 13 and 14, respectively, of Formulas 2, 3, 4, 5, 6, and (Ic), and C5 references carbon number 5 of Formulas 6 and (Ic).

13. The process of claim 12, wherein:
R[1] is selected from the group consisting of an alkyl group having from 1 to 8 carbon atoms, a vinyl group, an aryl group, cyclopropyl, cyclobutyl, {—}CH(CF$_3$)$_2$, {—}CH(CH$_3$)CF$_3$, {—}CH=CF$_2$, and {—}CH$_2$CF$_3$;
R[2] and R[3] are independently selected from the group consisting of hydrogen, halogen, OH, NH$_2$, CN, acyl, an alkyl, alkenyl, aryl, alkoxyl, and alkylamino;
R[4] is selected from the group consisting of hydrogen and alkyl;
R[5] and R[6] are independently selected from the group consisting of hydrogen, OH, and alkoxyl, wherein R[5] and R[6] together may form a group selected from the group consisting of =O, =NOH, and —O(CH$_2$)$_2$O—;
R[7] and R[8] are independently selected from the group consisting of hydrogen, OH and NH$_2$, wherein R[7] and R[8] together may form =O;
X is selected from the group consisting of bromide and chloride;
Y is selected from the group consisting of {—}CH$_2${—} and {—}CO{—}; and
Z is {—}O{—}.

14. The process of claim 13, wherein:
R[1] is cyclopropyl;
R[2] is hydrogen;
R[3] is {—}O(CH$_2$)$_m$CH$_3$;
R[5] and R[6] together form =O;
R[4], R[7], and R[8] are each hydrogen; and
m is an integer from 0 to 8.

15. The process of claim 12, wherein the weight ratio of compound 2 to vinyl chloroformate or 1-chloroethyl chloroformate to proton acceptor or proton donor is from about 1:2:1 to about 1:20:20, the reaction of Step A is conducted in the presence of an aprotic solvent, and at a temperature ranging from about 50° C. to about 120° C.; the weight ratio of compound 3 to R[1]YX or R[1]Y is from about 1:1 to about 1:3, the reaction of Step B is conducted in the presence of an aprotic solvent, and at a temperature ranging from about 20° C. to about 100° C.; the weight ratio of compound 4 to $X_2$ is from about 1:2 to about 1:2.5, the reaction of Step C is conducted in the presence of an organic solvent, and at a temperature ranging from about −30° C. to about 0° C.; the weight ratio of compound 5 to proton acceptor is from about 1:1.5 to about 1:20, the reaction of Step D is conducted in the presence of an aprotic and/or a protic solvent, and at a temperature ranging from about −30° C. to about 0° C.; and the weight ratio of compound 6 to scavenger to proton donor is from about 1:0.5:2 to about 1:2:20, the reaction of Step E is conducted in the presence of an aprotic solvent, and at a temperature ranging from about 0° C. to about 100° C.

16. The process of claim 15, wherein the proton acceptor has a pKa greater than about 13 and is selected from the group consisting of NaOH, KOH, LiOH, Ca(OH)$_2$, and NaH; the scavenger is an alcohol scavenger selected from the group consisting of $P_2O_5$, $POCl_3$, $POBr_3$, $PCl_3$, $PBr_3$, $SOCl_2$, $SOBr_2$, $MeSO_2Cl$, $(MeSO_2)_2O$, $SO_3$, $(CF_3SO_2)_2O$, and $(CF_3CO)_2O$; and the proton acceptor has a pKa less than about 0 and is selected from the group consisting of $MeSO_3H$, poly $H_3PO_4$, $H_3PO_4$, $H_2SO_4$, HCl, HBr, $HIO_4$, $HNO_3$, $CF_3SO_3H$, and p-methyltoluenesulfonic acid.

17. The process of claim 12, wherein the optical activity of compounds 2, 3, 4 and 5 is (−) or (+), and the configuration of C13, C14, and C9, respectively, is selected from the group consisting of RRS, RSS, SRR, and SSR.

18. The process of claim 12, wherein the optical activity of compounds 6 and (Ic) is (−) or (+), and the configuration of C5, C13, C14, and C9, respectively, is selected from the group consisting of RRRS, RRSS, SRRS, SRSS, RSRR, RSSR, SSRR, and SSSR.

19. The compound of claim 9, wherein $R^5$ and $R^6$ together form =O.

20. The compound of claim 9, wherein $R^5$ is OH.

21. The compound of claim 9, wherein $R^5$ is $NH_2$.

* * * * *